United States Patent [19]

Dahlquist et al.

[11] Patent Number: 4,678,915
[45] Date of Patent: Jul. 7, 1987

[54] SYSTEM AND PROCESS FOR MEASURING AND CORRECTING THE VALUES OF A PARAMETER OF A SHEET MATERIAL

[75] Inventors: John Dahlquist, Palo Alto; John Goss, San Jose; Gunnar Wennerberg, Cupertino, all of Calif.

[73] Assignee: Measurex Corporation, Cupertino, Calif.

[21] Appl. No.: 711,880

[22] Filed: Mar. 14, 1985

Related U.S. Application Data

[63] Continuation of Ser. No. 379,377, May 17, 1982, abandoned.

[51] Int. Cl.⁴ .................. G01N 27/72; G01R 33/00; G01F 23/00
[52] U.S. Cl. .................................. 250/358.1; 324/226
[58] Field of Search .............................. 324/225–227; 73/37.5–37.9; 250/358–360

[56] References Cited

U.S. PATENT DOCUMENTS

| | | | |
|---|---|---|---|
| 3,243,992 | 4/1966 | Woods | 324/231 |
| 3,757,126 | 9/1973 | Bossen et al. | 250/358.1 |
| 3,926,053 | 12/1975 | Shurrer et al. | 324/226 |
| 4,276,480 | 6/1981 | Watson | 250/560 |

Primary Examiner—Ernest F. Karlsen
Assistant Examiner—Walter E. Snow
Attorney, Agent, or Firm—Hal J. Bohner

[57] ABSTRACT

A system for measuring the values of a parameter of a sheet of material is provided. The system includes a head system with sensors mounted therein and a distance correction system to correct the measured parameter for variations in the distance between parts of the head system.

17 Claims, 9 Drawing Figures

SYSTEM AND PROCESS FOR MEASURING AND CORRECTING THE VALUES OF A PARAMETER OF A SHEET MATERIAL

This application is a continuation of application Ser. No. 379,377, filed May 17, 1982 now abandoned.

BACKGROUND OF THE INVENTION

1. The Field of The Invention

The present invention relates to an apparatus and process for measuring certain parameters of a sheet of material.

2. State of the Art

Systems are well known for measuring certain parameters of various sheet materials. For example, U.S. Pat. No. 3,757,122 teaches a system for measuring the basis weight of a moving sheet of paper. According to the patent, a gauging head is disposed with one part of the head on either side of the moving sheet of paper and the hed is mounted n a frame and adapted to travel in frame transversely of the sheet of paper. A radiation source is located in the lower head and a radiation detector is located in the upper head to receive radiation from the source. The amount of radiation received by the sensor is related to the basis weight of the paper, and thus the gauging system monitors the basis weight as the paper travels between the two heads.

Parameters other than the basis weight of paper can be measured by systems similar to the one described in U.S. Pat. No. 3,757,122. For example, U.S. Pat. No. 3,793,524 teaches a system for measuring the moisture content of a sheet of material such as paper. The system includes a source of infrared radiation located in a gauging head member disposed on one side of the sheet of material and a detector to receiver the radiation located in a head member disposed on the other side of the material. Other parameters of a sheet material such as opacity and thickness or caliper can also be measured by similar gauging systems.

In gauging systems of the type discussed above, we have found that the distance between the two gauging head parts can sometimes be significant in determination of the value of the parameter being measured. For example, in a system of the type discussed above to measure the basis weight of paper, we have found that measurement of the basis weight can be affected by the distance between the radiation source and the radiation detector even when the actual basis weight of the paper remains constant. We have also found that in practice, the distance between the two head members can sometimes vary in an unpredictable manner as they travel across the sheet of paper. Thus, the measured value of the basis weight can sometimes deviate from the actual value.

OBJECTS OF THE INVENTION

It is an object of the present invention to provide a system and process for measuring parameters of a sheet material wherein the measured value is corrected according to the separation of the head parts. It is a further object to provide a distance sensing system in a gauging system whereby the distance between the two parts of the gauging system head can be continuously measured, and means to apply the information developed from the distance sensing system to correct the measured value of a parameter.

Further objects and advantages of the present invention can be ascertained by reference to the drawings and specification hereof, which are offered by way of example and not in limitation of the invention which is defined by the claims and equivalents thereto.

DETAILED DESCRIPTION OF THE PREFERRED EMBODIMENTS

Figure 1:
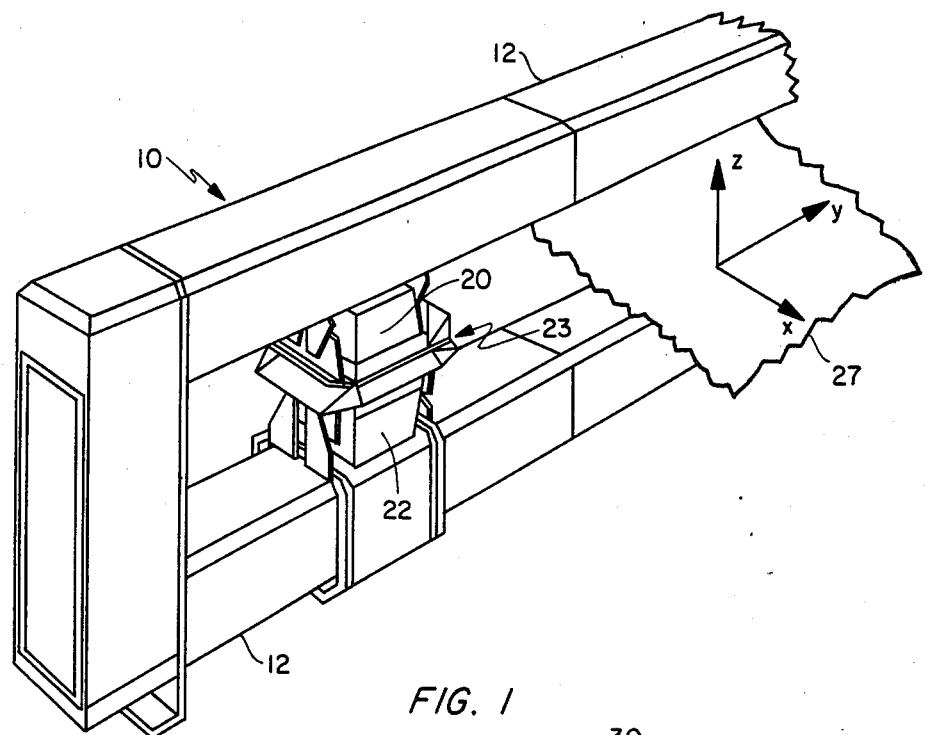
FIG. 1 illustrates a scanning system according to the present embodiment.

In FIG. 1 there is shown a scanner 10 which in operation would be disposed across one portion of a moving sheet of paper. The scanner includes two beams 12 disposed one above and one below the sheet of paper. A gauging head system includes an upper part 20 and lower part 22 mounted on the beams 12 so that they can move along the beams generally from left to right and right to left. A gap 23 is formed between the upper and lower parts 20 and 22 so that the paper 27 can be disposed in the gap 23. A co-ordinate system is shown on the paper indicating the machine or "X" direction, the cross-machine or "Y" direction and the "Z" direction which is perpendicular to the "X" and "Y" directions.

Figure 2:
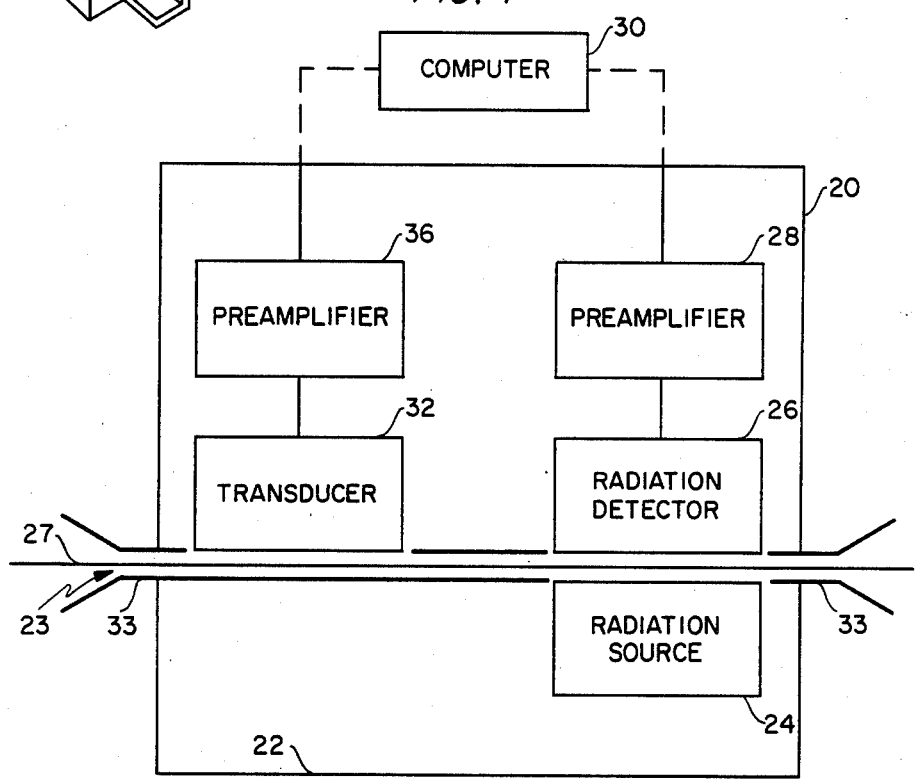
FIG. 2 is a schematic illustration of one part of the present embodiment.

With reference to FIG. 2, the parts 20 and 22 include a sensor system comprising a radiation source 24 and radiation detector 26. The radiation source is located in the lower part 22 and emits beta radiation which passes through the paper 27. The beta radiation from the source 24 is in the form of particles generated by a succession of events due to radioactive decay. In some applications, alpha, gamma, and x-ray radiation are also feasible. The radiation detector 26 is located in the upper part 20 and is capable of sensing radiation from the source 24. The radiation detector receives radiation from the source 24 and produces an electrical signal in response to the amount of radiation received. A preamplifier 28 is coupled to receive the electrical signals from the detector 26 and to amplify the signals so that they can be transmitted to a computer 30.

The scanner and sensor systems described thus far can be of the type taught in U.S. Pat. No. 3,757,122. The patent teaches that the intensity of radiation received by the detector is related to the basis weight of the paper by the formula $I = I_o e^{-ux}$. In the formula $I_o$ is the intensity of radiation reaching the detector when there is no sheet material in the gap; u is the mass absorption coefficient; x is the weight per unit area of the sheet material being measured; and I is the intensity of received radiation when the sheet material is in the gap. We have found that this formula can be used if the radiation source and detector are spaced a constant distance from one another and the system is calibrated with the source and detector a predetermined distance from one another. However, in practice we have found that the separation between the beams 12 of the scanner 10 is not precisely the same throughout the length of the beams. Consequently, as the heads move along the beams the separation between the heads will change. Also, we have found that in practice the beams and the head system can change temperature during operation. For example, in the paper making process the paper is often quite hot, which causes the scanner to be hot. However, if the paper breaks and the process is shut down for some time, the scanner system can become relatively cool. When the process resumes, the scanner begins to heat due to the heat of the paper. Thus the scanner beams 12 can deform slightly so that as the beams 12 get warmer, the spacing between the parts 20 and 22 of the head system changes. Consequently, we have found that in some applications it is important to correct the measured values of the basis weight as measured by the radiation detectors to account for the variability in the distance between the head parts.

The parts 20 and 22 contain distance sensing means comprising a transducer 32 affixed to the upper part 20 and reference means affixed to the lower part 22. Transducer 32 is spaced apart from the lower part 22 and moves with the head system. The transducer is located near the face 33 of the upper head part so that the distance to the lower part 22 is minimized. The transducer 32 generates an electrical signal according to the distance between the transducer 32 and the reference means affixed to the lower part 22. The transducer 32 is connected to a preamplifier 36 which is in turn connected to the computer 30.

Figure 3:
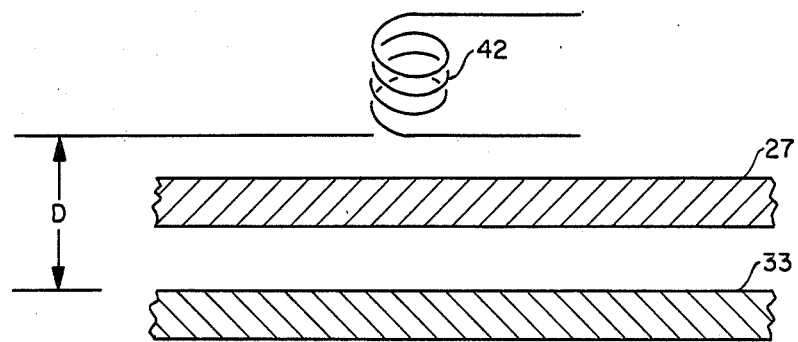
FIG. 3 is a schematic illustration of a detail of part of one embodiment of the present invention.

We have found that a suitable distance sensing means can be of the type described in U.S. Pat. No. 4,160,204 titled "Non-Contact Distance Measurement System". With reference to FIG. 3, the distance sensing means includes a coil 42 located in the upper head part 20 and face 33 of the lower head part 22. The coil 42 is coupled to an electrical circuit, not shown, to measure the current in the coil. The impedance of the coil is related to the distance between the coil 42 and the face 33.

Figure 4:
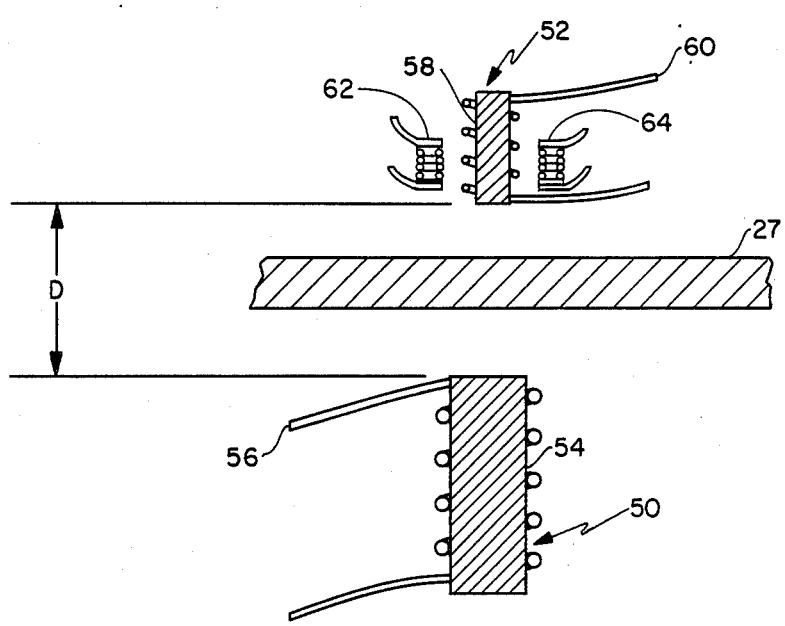
FIG. 4 is a schematic illustration of a detail of part of another embodiment of the present invention.

Alternatively, the distance measuring system can be as illustrated in FIG. 4. According to FIG. 4, there is a transmitter 50 and a receiver 52. The transmitter 50 includes a first member 54, substantially cylindrical in shape, of a magnetically susceptible material such as iron. Wound around the first member 54 is a first wire 56. The transmitter 50 is positioned such that the axis of the first member 54 is substantially perpendicular to the sheet of paper. The receiver 52 comprises a second member 58, substantially cylindrical in shape, also of a magnetically susceptible material. Wound around the second member 58 is a second wire 60. The member 58 is positioned such that the axis of the second member 58 is substantially aligned with the axis of the first member 54. A source of alternating current, not shown, is coupled to the first wire 56 so that when current is passed through the wire, a magnetic field with a varying amplitude is generated by the transmitter 50. The magnetic field induces a second magnetic field in the second member 58, and the intensity of the magnetic field is a function of the distance between the transmitter 50 and the receiver 52. As the distance between the transmitter and the receiver increases, the amplitude of the magnetic field sensed by the receiver decreases.

The distance measuring system in FIG. 4 includes two small coils of wire 62 and 64 disposed adjacent the receiver 52. The transmitter 50 induces magnetic fields in the coils 62 and 64, and the magnitude of the induced field depends upon the distance between the transmitter 50 and a particular coil. Thus it can be determined when the transmitter 50 and receiver 52 are not aligned with one another. In some circumstances misalignment could result in inaccurate measurement of "D;" however, the coils 62 and 64 can be used to correct for such inaccuracies. The coils 62 and 64 can be located that they are in the "X" or "Y" direction relative to the receiver 52, depending upon the direction of misalignment which is of interest. Also, two coils can be located in the "X" direction and two in the "Y" direction to permit measurement of misalignment in both directions.

It can be seen that the system shown in FIG. 3 does not include small coils 62 and 64 shown in FIG. 4. Such small coils are not utilized in the FIG. 3 system because in the FIG. 3 system, if the transducer 42 moves left or right but the distance D remains constant, the output of the transducer remains constant. Thus the system accurately measures displacement in the "Z" direction even though there may be misalignment in the "X" or "Y" direction.

Figure 5:
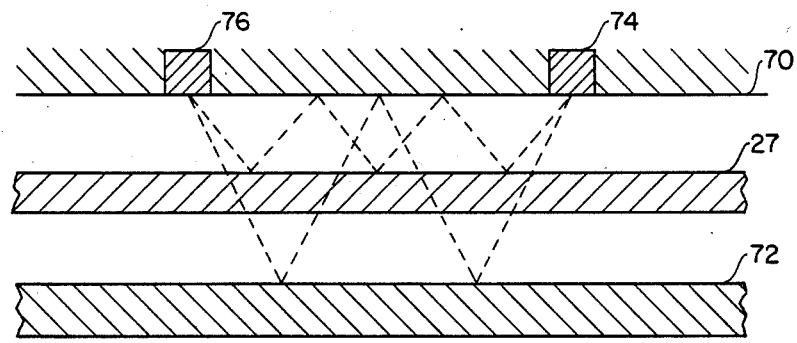
FIG. 5 is a schematic illustration of a detail of an embodiment of the present invention.

The system described above is for measuring the basis weight of paper. However, it should be understood that the present invention can also be utilized in the measurement of other parameters of sheet material. For example, in FIG. 5 there is illustrated part of a system for measuring the moisture content of a sheet of paper. Such a system is taught in U.S. Pat. No. 3,793,524. The system will not be described in detail herein, and for further description of the system reference is made to the patent. The system includes upper and lower paper guides 70 and 72, respectively, which can be mounted on the faces 33 of the upper and lower head parts 20 and 22, or the guides can be integral with the parts 20 and 22. The guides 70 and 72 have reflective surfaces which can be formed by polishing or in other ways as taught in the patent. A source of infrared radiation 74 is disposed in the upper guide 70, and a detector to detect the radiation is also mounted in the upper guide 70 to receive radiation from the source 74. Radiation from the source 74 is reflected from the surfaces of the guides 70 and 72, and the radiation is in part transmitted through the paper while part is reflected from the paper, as illustrated by the dotted lines. Measurement of the radiation received by the detector 76 is utilized to determine the moisture content of the paper.

In operation, the head system scans back and forth across the paper which is moving transversely to the scanning direction. Meanwhile, as a parameter of the paper such as basis weight or moisture content is being measured, the distance sensing means is measuring the distance between the heads, and the measured values of the parameter and the distance are transmitted to the computer 30. The distance between the heads can vary during the operation of the system and the system automatically corrects the measured parameter to account for the variability in the distance between the heads. In certain applications the basis weight and the distance between the sensors can be measured periodically at a predetermined time interval. Thus, both measurements are in fact a series of values representing the basis weight and the distance between the heads at specific points in time and at specific points on the paper. In practice, these points can be made close together to provide virtually continuous measurement.

As mentioned above, we have found that as the head system scans across the paper sheet there are two primary sources of variability of the distance between the head parts. In particular, separation can vary because the beams 12 of the scanner are not spaced apart the same distance throughout their length. Also, during operation of the system the head system and the beams can heat up thereby causing the distance between the head parts to change over time. An illustration of some of our test results verifying the heating effect is shown in FIG. 6.

Figure 6:
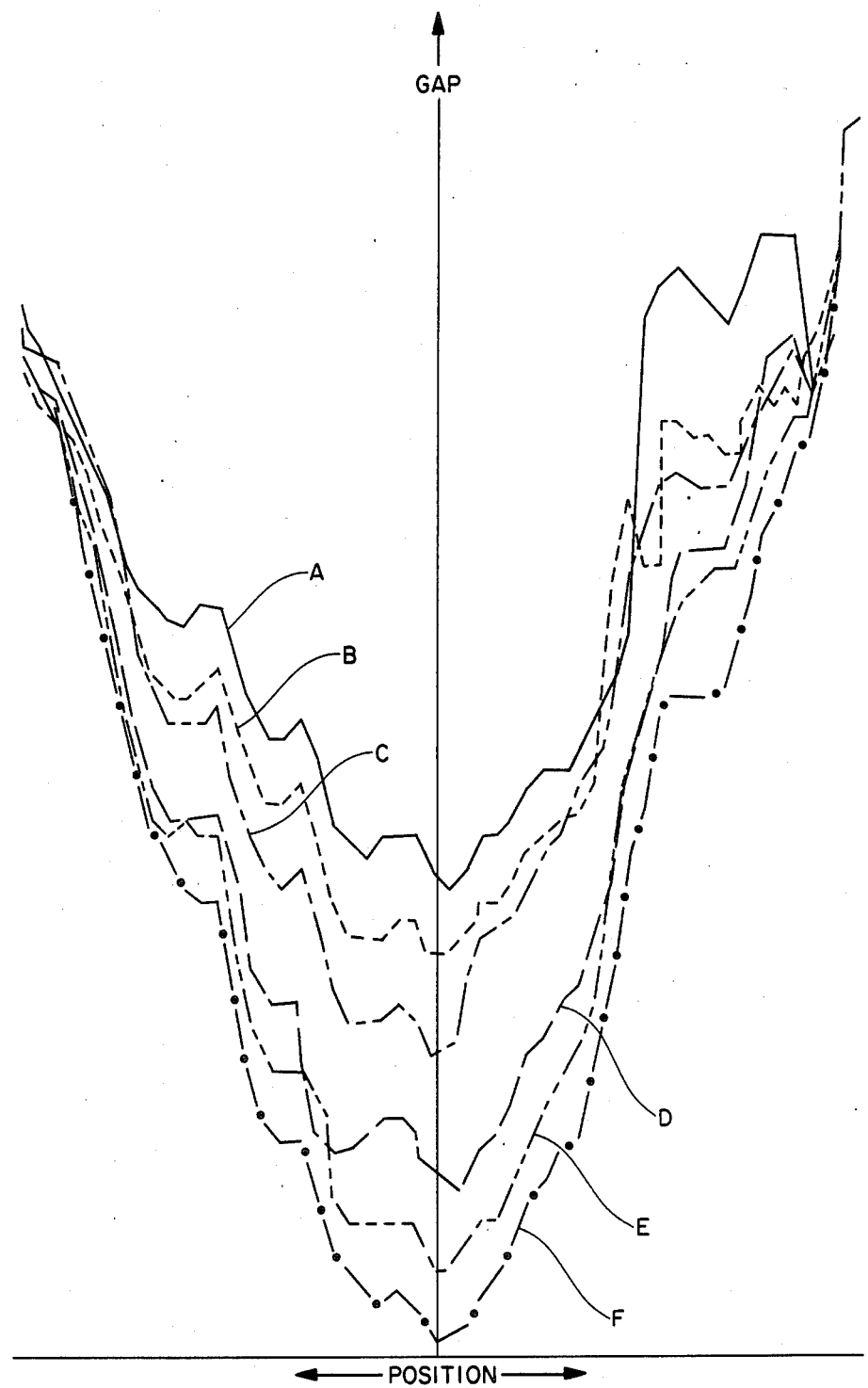
FIG. 6 is a graph illustrating one of the problems the present system is designed to overcome.

FIG. 6 is a plurality of graphs, each of which indicates the separation between the parts of the head system at a particular time along the length of the scanner. (It should be noted that the graphs are not to scale and that the "Position" axis does not represent zero separation.) To develop these graphs, we operated a scanner from a cold start and measured the separation between the head parts with the present system as the system heated up. Curve A illustrates the separation of the head parts throughout the length of the scanner at the beginning of the run when the system was relatively cool. As can be seen from the curve A, the distance between the head parts was greater when the head system was near the ends of the scanner than when the system was near the center of the scanner. Also, it should be noted that the curve is not smooth but that there are certain local irregularities in the distance between the head parts. Curve B illustrates the separation of the head parts five minutes after the curve A was developed. It can be seen that in curve B the separation of the head parts throughout the length of the scanner is somewhat less than the separation of the head parts shown in curve A. This illustrates the effect of heating upon the system. In general, the same local irregularities throughout the curve as were found in curve A are also found in curve B. Curves C through F were taken at progressively later times (from about 5 to 30 minutes between curves), and the progression of the curves indicates that the separation between the head parts generally decreased as the system heated up. Also, it should be noted that the local irregularities in the curves are not constant through time but change somewhat as the system heats up. Furthermore, the local irregularities can change rapidly. Thus, it can be appreciated that it is important that the present system can continuously measure the distance between the head parts and compensate for the variability in distance.

Figure 7:
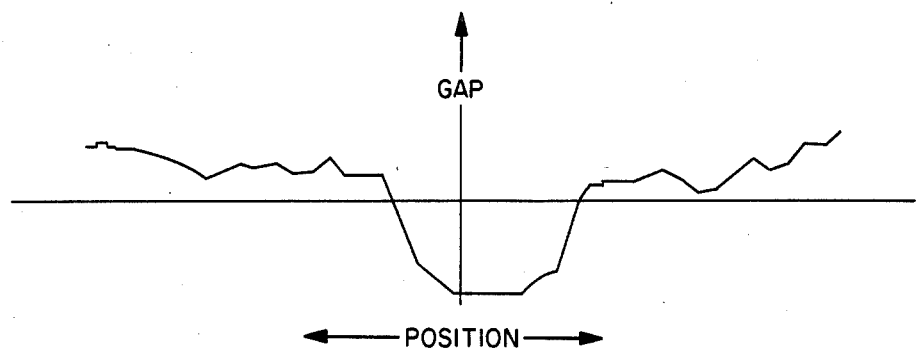
FIGS. 7-9 are graphs illustrating the operation of an embodiment of the present invention.
Figure 8:
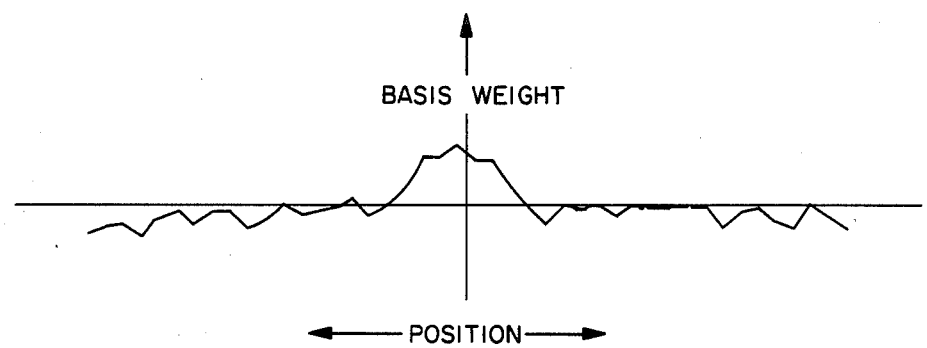
Figure 9:
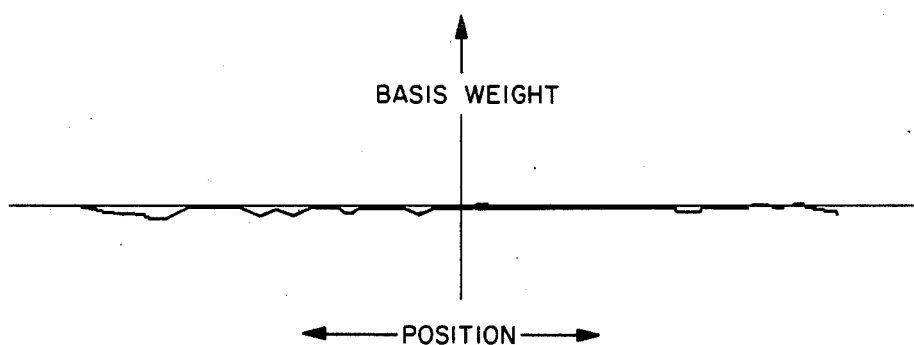

FIGS. 7-9 illustrate an example of a test we have conducted showing the effectiveness of the present system in correcting for variation between the head parts. FIG. 7 is a graph of the position across the scanner versus the separation of the head parts. In this test, we altered the scanner to reduce the distance between the parts, i.e., the gap, substantially near the middle of the scanner, and this reduction in the gap is illustrated as a large "bump" in the middle of the graph. FIG. 8 shows the position across the scanner versus the measured basis weight of the paper without the application of the present invention. As can be seen, the measured basis weight of the paper increases dramatically at the location of the "bump." However, we know from other tests that in fact the basis weight of the paper did not increase toward the center of the scanner.

FIG. 9 illustrates the operation of the present system. The graph shows the measured basis weight across the scanner and illustrates that with the correction applied to compensate for the "bump" in the middle of the scanner, the basis weight does not show a large increase in the center of the sheet of paper.

The system described above and shown in FIG. 1 includes a scanner wherein the head parts 20 and 22 are movable relative to the beams 12. It should be understood that the present invention is also applicable to other types of scanning systems such as so-called C-frame systems in which the head parts are rigidly affixed to a frame.

Furthermore, the embodiments discussed above include two head parts 20 and 22. However, the present invention is also applicable to a system including a single head member disposed on one side of the paper. Such an embodiment includes a fixed member such as a roller or a low-friction, plastic guide disposed on the opposite side of the paper and spanning the full width of the paper. This embodiment would be appropriate for utilization with an x-ray backscatter-type sensor, for example. In such an embodiment the fixed member would support the paper across the width thereof and would provide a reference point for measuring distance from the transducer 32.

We claim:

1. A process for measuring the values of a parameter of a sheet of material at various points by a sensor system including a first head member and a second head member and for correcting the measured values of the parameter to account for variability of the separation of the head members from one another without determining the separation of either head member from the sheet, the process comprising;
   (a) measuring the values of the parameter with the sensor system without correction for variability of the separation of the head members from one another to provide uncorrected, measured values;
   (b) determining the separation of the head members from one another by transmitting a signal through the sheet but not determining the separation of the head members from the sheet; and,
   (c) correcting the uncorrected measured values according to the separation of the head members from one another, but not according to the separation of the head members from the sheet.

2. A process according to claim 1 wherein the sheet of material is traveling in a first direction, the first head member and the second head member travel in a second direction which is perpendicular to the first direction, and the correction is made based upon separation of the head members only in the "Z" direction which is orthogonal to the first and second directions.

3. A process according to claim 1 wherein the sheet of material is traveling in a first direction, the first head member and the second head member travel in a second direction which is perpendicular to the first direction, and the correction is made based upon separation of the head members in a direction other than the "Z" direction wherein the "Z" direction is orthogonal to the first and second directions.

4. A process according to claim 1 wherein the separation of the head members from one another is determined by electromagnetic induction.

5. A process according to claim 1 wherein the separation of the head members from one another is determined while the values are being measured.

6. A process according to claim 1 wherein the separation of the head members from one another is determined when the head members are at a plurality of positions, each of said positions corresponding to a position at which a value of the parameter is measured.

7. A system for measuring the values of a parameter of a sheet of material at various points by a sensor system including head means and for correcting the measured values of the parameter to account for variability of the separation of parts of the head means without measuring the distance from the sensor system to the sheet, the system comprising;
  (a) head means having a first part disposed on a first side of the sheet and a second part disposed on a second side of the sheet;
  (b) distance sensing means coupled to the head means to measure the distance between the two parts of the head means by transmitting a signal through the sheet;
  (c) sensor means coupled to the head means for measuring the values of a parameter of the sheet but not the distance between said sensor means and the sheet to produce uncorrected, measured values;
  (d) parameter determination means coupled to receive signals from the sensor means and from the distance sensing means for correcting the uncorrected, measured values according to the distance between said two parts of said head means but not according to the distance between the head means and the sheet.

8. A system according to claim 7 wherein the sensor means includes a source located in said first part of said head means and a detector located in said second part of said head means.

9. A system according to claim 7 wherein the sensor means includes a source and a detector both located in one part of said head means.

10. A system according to claim 7 wherein the distance sensing means includes a transducer mounted in one part of the head means.

11. A system according to claim 7 wherein the distance sensing means includes a transmitter mounted in one part of the head means and a receiver mounted in the other part of said head means.

12. A system according to claim 11 wherein the transmitter generates a magnetic field.

13. A system according to claim 11 wherein the signal from the transmitter is substantially unaffected by the sheet of material.

14. A system according to claim 7 wherein said second part is spaced apart from the sheet.

15. A system according to claim 7 wherein the sensor system measures at least one parameter other than thickness of the sheet.

16. A system according to claim 15 wherein the sensor system measures the basis weight of the sheet.

17. A system according to claim 15 wherein the sensor system measures the moisture of the sheet.

* * * * *

REEXAMINATION CERTIFICATE (2952th)
United States Patent [19]
Dahlquist et al.

[11] B1 4,678,915
[45] Certificate Issued Jul. 16, 1996

[54] SYSTEM AND PROCESS FOR MEASURING AND CORRECTING THE VALUES OF A PARAMETER OF A SHEET MATERIAL

[75] Inventors: John Dahlquist, Palo Alto; John Goss, San Jose; Gunnar Wennerberg, Cupertino, all of Calif.

[73] Assignee: Measurex Corporation, Cupertino, Calif.

Reexamination Request:
No. 90/003,687, Jan. 12, 1995

Reexamination Certificate for:
Patent No.: 4,678,915
Issued: Jul. 7, 1987
Appl. No.: 711,880
Filed: Mar. 14, 1985

Related U.S. Application Data

[63] Continuation of Ser. No. 379,377, May 17, 1982, abandoned.

[51] Int. Cl.$^6$ .......................... G01N 27/72; G01R 33/00; G01F 23/00
[52] U.S. Cl. .......................... 250/358.1; 324/226
[58] Field of Search .......................... 324/226, 227, 324/229, 230, 231, 262; 250/252.1, 358.1, 308, 359.1, 360.1; 73/159

[56] References Cited

U.S. PATENT DOCUMENTS

| | | | |
|---|---|---|---|
| 2,884,535 | 4/1959 | Swift, Jr. | 250/83.6 |
| 3,125,680 | 3/1964 | Schlaechter | 250/106 |
| 3,185,843 | 5/1965 | Hansen | 250/83.3 |
| 3,237,446 | 3/1966 | Wood | 73/67.9 |
| 3,306,103 | 2/1967 | Davis | 73/159 |
| 3,348,057 | 10/1967 | Burroughs . | |
| 3,479,511 | 11/1969 | Clere | 250/83.6 |
| 3,536,405 | 10/1970 | Flower . | |
| 3,552,203 | 1/1971 | Frech . | |
| 3,586,972 | 6/1971 | Tulleners | 324/61 |
| 3,606,541 | 9/1971 | Sugano et al. | 356/120 |
| 3,655,979 | 4/1972 | Jernigan, Jr. | 250/83.3 |
| 3,667,283 | 6/1972 | Takenaka et al. | 73/37.7 |
| 3,681,595 | 8/1972 | Dahlin | 250/83 C |
| 3,793,524 | 2/1974 | Howarth | 250/339 |
| 3,879,614 | 4/1975 | Martin | 250/548 |
| 3,884,076 | 5/1975 | Studer | 73/37.6 |
| 3,909,615 | 9/1975 | Bosch . | |
| 3,913,012 | 10/1975 | Kujath . | |
| 3,936,189 | 2/1976 | De Remigis . | |
| 3,997,768 | 12/1976 | de Feo | 235/151.1 |
| 4,068,955 | 1/1978 | Bodlaj . | |
| 4,102,578 | 7/1978 | Suzuki et al. | 356/120 |
| 4,160,204 | 7/1979 | Holmgren et al. | 324/207 |
| 4,167,878 | 9/1979 | Bottcher et al. | 73/601 |
| 4,208,581 | 6/1980 | Kaneko | 250/277 R |
| 4,276,480 | 6/1981 | Watson | 250/358.1 |
| 4,300,049 | 11/1981 | Sturm | 250/339 |
| 4,311,392 | 1/1982 | Yazaki et al. | 356/375 |
| 4,450,404 | 5/1984 | Williams et al. | 324/226 |

FOREIGN PATENT DOCUMENTS

| | | | |
|---|---|---|---|
| 0078096 | 5/1983 | European Pat. Off. . | |
| 0094669 | 11/1983 | European Pat. Off. | 250/308 |
| 2219412 | 9/1974 | France . | |
| 1807600 | 7/1971 | Germany . | |
| 2355185 | 11/1973 | Germany . | |
| 43-23159 | 10/1943 | Japan . | |
| 49-65252 | 6/1974 | Japan . | |
| 53-42762 | 4/1978 | Japan . | |
| 54-66167 | 5/1979 | Japan . | |
| 598972 | 2/1978 | U.S.S.R. . | |
| 1151379 | 5/1969 | United Kingdom . | |
| WO81/02628 | 9/1981 | WIPO . | |

*Primary Examiner*—Walter E. Snow

[57] ABSTRACT

A system for measuring the values of a parameter of a sheet of material is provided. The system includes a head system with sensors mounted therein and a distance correction system to correct the measured parameter for variations in the distance between parts of the head system.

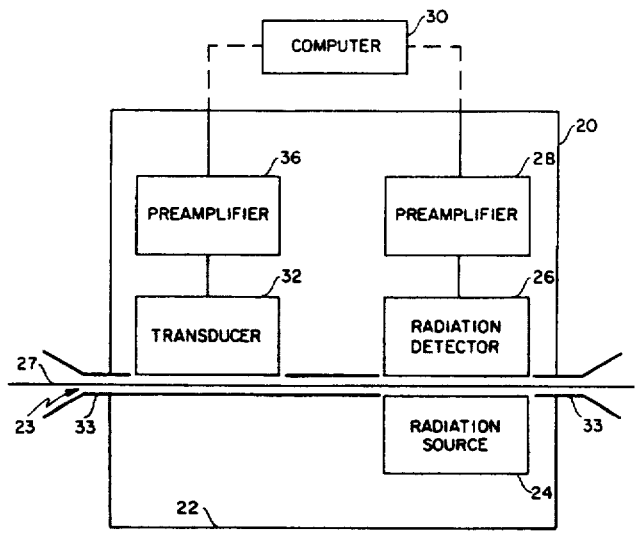

B1 4,678,915

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 1–8 and 10–17 is confirmed.

Claim 9 is cancelled.

New claims 18–47 are added and determined to be patentable.

18. A process according to claim 1, wherein the step of measuring the values of the parameter further includes steps of:

generating particles due to radioactive decay from a radiation source;

receiving radiation from the radiation source at a radiation detector; and producing an electrical signal in response to an amount of the received radiation.

19. A process according to claim 18, wherein said step of receiving further includes a step of:

sensing particles from said radiation source which pass through said sheet of material.

20. A process according to claim 18, further including a step of:

relating an intensity of the received radiation to a basis weight of the sheet of material.

21. A process according to claim 20 wherein said step of relating further includes a step of:

using a formula:

$$I = I_o e^{-ux}$$

wherein I is the intensity of received radiation, $I_o$ is an intensity of radiation received when there is no sheet of material between the radiation source and the radiation detector, u is a mass absorption coefficient, and x is a weight per unit area of the sheet of material.

22. A process according to claim 21, wherein said step of generating further includes a step of:

emitting beta radiation from said radiation source.

23. A process according to claim 1, wherein said step of measuring further includes a step of:

moving said sheet of material in a first direction; and scanning said sheet of material in a scanning direction which is transverse to said first direction, said step of correcting being performed while said values are being measured during the step of scanning.

24. A process according to claim 1, wherein said step of determining further includes a step of:

measuring current in a transducer affixed to one of said head parts to determine the separation of the head parts from one another.

25. A process according to claim 1, wherein said step of determining further includes the step of:

generating an electrical signal proportional a distance between said first head part and said second head part for use in said step of correcting.

26. A process according to claim 19, further comprising a step of:

transmitting at least one additional signal for reflection by said sheet of material.

27. A process according to claim 26, wherein said at least one additional signal is infrared radiation used to determine moisture content of said sheet of material.

28. A process for measuring the values of a parameter of a sheet of material at various points by a sensor system including a first head part and a second head part and for correcting the measured values of the parameter to account for variability of the separation of the head parts from one another without determining the separation of either head part from the sheet, the process comprising:

(a) measuring the values of the parameter with the sensor system without correction for variability of the separation of the head parts from one another to provide uncorrected, measured values, said step of measuring further including the steps of:

generating particles due to radioactive decay from a beta radiation source;

receiving radiation from the radiation source of a radiation detector by sensing particles from said radiation source which pass through said sheet of material; and relating an intensity of the received radiation to a basis weight of the sheet of material;

(b) determining the separation of the head parts from one another by transmitting a signal through the sheet but not determining the separation of the head parts from the sheet; and, (c) correcting the uncorrected measured values according to the separation of the head parts from one another, but not according to the separation of the head parts from the sheet.

29. A process according to claim 28 wherein said step of relating further includes a step of:

using a formula:

$$I = I_o e^{-ux}$$

wherein I is the intensity of received radiation, $I_o$ is an intensity of radiation received when there is no sheet of material between the radiation source and the radiation detector, u is a mass absorption coefficient, and x is a weight per unit area of the sheet of material.

30. A process according to claim 29, wherein said step of measuring further includes a step of:

moving said sheet of material in a first direction; and scanning said sheet of material in a scanning direction which is transverse to said first direction, said step of correcting being performed while said values are being measured during the step of scanning.

31. A process according to claim 30, further comprising a step of:

transmitting at least one additional signal for reflection by said sheet of material.

32. A process according to claim 31, wherein said at least one additional signal is infrared radiation used to determine moisture content of said sheet of material.

33. A system according to claim 8, wherein said sensor means further includes:

a radiation source for generating particles due to radioactive decay; and a radiation detector for sensing radiation from the radiation source.

34. A system according to claim 33, wherein said parameter determination means further includes:

a computer for calculating said measured values of said sheet of material in response to an amount of radiation passed through said sheet of material and received by said radiation detector.

35. A system according to claim 33, wherein said parameter determination means further includes:

a computer for relating an intensity of the received radiation to a basis weight of the sheet of material using the formula:

$$I = I_o e^{-ux}$$

wherein $I$ is the intensity of received radiation, $I_o$ is an intensity of radiation received when there is no sheet of material between the radiation source and a radiation detector, $u$ is a mass absorption coefficient, and $x$ is a weight per unit area of the sheet of material.

36. A system according to claim 8, wherein said sensor means further includes:

a radiation source located in said first part of said head means for generating particles due to radioactive decay, said head means being located on a first side of said sheet of material; and a radiation detector located on a second side of said sheet of material, opposite said first side, for receiving particles from said radiation source which pass through said sheet of material.

37. A system according to claim 36, further comprising:

an additional radiation source for transmitting at least one additional signal which is reflected by said sheet of material.

38. A system according to claim 37, wherein said at least one additional signal is infrared radiation used to determine moisture content of said sheet of material.

39. A system according to claim 8, wherein said distance sensing means further includes:

a transducer affixed to one of said first part and said second part, and a reference means affixed to the other of said first part and said second part, said transducer including a coil having an impedance related to a distance between said first part and said second part.

40. A system according to claim 39, wherein said distance sensing means further includes:

at least one additional coil disposed adjacent said transducer coil for determining when said transducer coil and said reference means are out of alignment with one another.

41. A system according to claim 8, wherein said sensor means includes:

a radiation source of emitting beta radiation.

42. A system according to claim 8 wherein said sheet of material is movable in a first direction and said head means is mounted for scanning said sheet of material in a scanning direction which is transverse to said first direction, said parameter determination means further including:

a computer for correcting the uncorrected, measured values of said sheet of material during scanning of said sheet of material by said head means.

43. A system for measuring the values of a parameter of a sheet of material at various points by a sensor system including head means and for correcting the measured values of the parameter to account for variability of the separation of parts of the head means without measuring the distance from the sensor system to the sheet, the system comprising:

(a) head means having a first part disposed on a first side of the sheet and a second part disposed on a second side of the sheet;

(b) distance sensing means coupled to the head means to measure the distance between the two parts of the head means by transmitting a signal through the sheet;

(c) sensor means coupled to the head means for measuring the values of a parameter of the sheet but not the distance between said sensor means and the sheet to produce uncorrected, measured values, said sensor means including:

a radiation source for generating particles due to radioactive decay; and a radiation detector for sensing radiation from the radiation source;

(d) parameter determination means coupled to receive signals from the sensor means and from the distance sensing means for correcting the uncorrected, measured values according to the distance between said two parts of said head means but not according to the distance between the head means and the sheet, said parameter determination means further including:

a computer for calculating a basis weight of said sheet of material in response to an amount of radiation passed through said sheet of material and received by said radiation detector.

44. A system according to claim 43, wherein said sensor means includes:

a radiation source for emitting beta radiation.

45. A system according to claim 44, further comprising:

an additional radiation source for transmitting at least one additional signal which is reflected by said sheet of material.

46. A system according to claim 45, wherein said at least one additional signal is infrared radiation used to determine moisture content of said sheet of material.

47. A system according to claim 46, wherein said sheet of material is movable in a first direction, said system further including:

a mount for scanning said head means back and forth across said sheet of material in a scanning direction which is transverse to said first direction, with said sensor means measuring said parameter values during said scanning, with said distance sensing means measuring said distance between the two parts during said scanning, and with said parameter determination means correcting the uncorrected, measured values during said scanning.

* * * * *